US006171602B1

(12) United States Patent
Roman

(10) Patent No.: US 6,171,602 B1
(45) Date of Patent: Jan. 9, 2001

(54) NATURAL PIGMENT-CONTAINING FLOWABLE POWDER

(75) Inventor: Frank Roman, Garden City, NY (US)

(73) Assignee: E-L Management Corp., New York, NY (US)

( * ) Notice: Under 35 U.S.C. 154(b), the term of this patent shall be extended for 0 days.

(21) Appl. No.: 08/920,510

(22) Filed: Aug. 29, 1997

(51) Int. Cl.⁷ ............................. A61K 6/00; A61K 7/00; A61K 7/42; A61K 7/44
(52) U.S. Cl. ............................. 424/401; 424/59; 424/60; 424/63; 424/69; 514/844; 514/846
(58) Field of Search ................. 424/401, 59, 63, 424/69, 60; 514/844, 846

(56) References Cited

U.S. PATENT DOCUMENTS

| 4,783,333 | 11/1988 | Mercado et al. |
|---|---|---|
| 4,820,508 | 4/1989 | Wortzman. |
| 4,822,600 | 4/1989 | Wortzman. |
| 5,688,831 | * 11/1997 | El-Nokaly ............................ 514/938 |
| 5,747,049 | * 5/1998 | Tominaga ............................ 424/401 |

FOREIGN PATENT DOCUMENTS

| 0 212 870 | 3/1987 | (EP) . |
|---|---|---|
| 0 266 248 | 5/1988 | (EP) . |
| 0 587 908 | 3/1994 | (EP) . |
| 2 432 035 | 2/1980 | (FR) . |
| 2030161 | 2/1980 | (GB) . |
| 57-140948 | 8/1982 | (JP) . |
| 1-180812 | 8/1989 | (JP) . |

* cited by examiner

Primary Examiner—Theodore J. Criares
(74) Attorney, Agent, or Firm—Dorene M. Price, Esq.; Karen A. Lowney, Esq.

(57) ABSTRACT

The present invention relates to a method for preparing a stable natural pigment composition comprising combining (a) a liquid hydroalcoholic base containing a natural pigment, a UV absorber, and an antioxidant, with (b) an absorbent base containing a porous bead, and allowing the absorbent base to absorb the liquid base. The invention also relates to the natural pigments per se as well as cosmetic compositions containing them.

28 Claims, No Drawings

NATURAL PIGMENT-CONTAINING FLOWABLE POWDER

FIELD OF THE INVENTION

The present invention relates to natural pigments. In particular, the invention relates to natural pigments which have been stabilized so as to be useful in cosmetic compositions.

BACKGROUND OF THE INVENTION

The use of colorants derived from plants or other pigmented natural resources goes back thousands of years in human history. Such pigments were widely used for dyes, and to some extent, for facial adornment. Since the preparation of any type of pigment-containing product was necessarily done on a short-term, small-scale basis in the ancient world, however, the inherent difficulties associated with the use of these materials, particularly with regard to stability, presented little concern.

What was acceptable in biblical times, however, is not acceptable today. Color cosmetics are now the basis for a huge industry, and preparation of these compositions is no longer relegated to the royal cosmetician or the local apothecary. The products sold today must meet high governmental regulatory standards, must have a reasonable compatibility with a wide variety of solvent systems and formulation variations, and particularly must be able to withstand the rigors of long-term storage and transportation. As most, if not all, natural pigments have a tendency to bleed, fade, or otherwise deteriorate in a very short period of time, the requirements of modern cosmetics cannot be met by their use. Therefore, the cosmetics industry has turned primarily to the use of inorganic pigments, such as metal oxides, or synthetic organic pigments, which can withstand assaults on stability, such as water, oxidation, light and temperature extremes. Even these pigments have their own share of stability problems; nonetheless, they are, overall, much more stable than the average natural pigment. Notwithstanding the superior stability and general flexibility of the oxides and synthetic pigments, however, consumers are now increasingly demanding a return to what are perceived as more "natural" products. To meet this demand, therefore, there is a continuing need to find ways to enhance the stability of naturally occurring pigments, to the extent that they can be used in cosmetics that can be stored for long periods, yet retain their color and not add significantly to the cost of the final product.

There have been many reports in the industry as to methods for stabilizing natural pigments. However, to date, none have found widespread commercial application in the cosmetics industry, perhaps because many are designed for use only with a specific kind of pigment, and the resulting pigment is useful only with one particular kind of solvent system. Therefore,

SUMMARY OF THE INVENTION

The present invention provides a method for producing a stable natural pigment, the method comprising mixing (a) a liquid hydroalcoholic base containing a natural pigment, a UV absorber, and an antioxidant, with (b) an absorbent base comprising a porous bead; and drying the mixture to obtain the stable pigment. The invention also relates to the stable pigment obtained therefrom. Also provided are cosmetic compositions containing the natural pigments.

DETAILED DESCRIPTION OF THE INVENTION

The initial step in preparing the compositions of the invention is the preparation of a hydroalcoholic base, in which are solubilized the pigment, a UV absorber, and an antioxidant. The hydroalcoholic base allows the solubilization in a single solution of both hydrophilic and lipophilic components. Although suggested amounts of each material are provided in the discussion below, it will be understood that these amounts are provided primarily as guidelines, and it is within the ability of the skilled artisan to modify amounts when required due to the particular activity or potency of a chosen component. The alcohol employed is one which will permit solubilization of both types of components, and is preferably a short chain alcohol, i.e., $C_2$–$C_4$. Particularly preferred is ethanol. The alcohol is present in an amount of from about 20–40% of the base as a whole, and water generally comprises from about 20–55% of the base.

Most of the natural colors which are of interest for cosmetic use are water soluble. The natural water-soluble pigments are mixed directly into the water component, typically in an amount of from about 1–20%, the concentration being largely dependent upon the intensity of color desired. Obviously, any non-water-soluble pigments are mixed into the alcohol phase of the liquid base. Any natural pigment may be used in this process; however, it is preferred that the pigment be one which is cosmetically acceptable; by "cosmetically acceptable" is meant one which does not cause harm to human skin. Among the pigments that can be used in the present method are, for example, annatto extract, B-Apo-8-carotenal, azulene, beta-carotene, beet powder, canthaxanthin, caramel color, carrot oil, cochineal extract (carmine), cotton seed flour, ferrous gluconate, fruit juice, grape color extract, grape skin extract(ecociannina), paprika, riboflavin, saffron, titanium dioxide, turmeric, turmeric oleoresin, vegetable juice, chlorophyll, guaizulene, and red cabbage.

At least one UV-absorber is also added to the hydroalcoholic base. The UV absorbing compound can be any material which is cosmetically acceptable. Among those that can be used in the present pigment compositions are salicylates, para-amino benzoic acid(PABA) and derivatives thereof, amino benzoates, benzophenones, ferulic acid, digalloyl trioleate, cinoxate, cinnamates, and anthranilates. Particularly preferred are benzophenones. The UV absorber can be used in an amount of from about 0.5–10% by weight of the total composition, preferably in an amount of from about 1–3%.

Also incorporated into the hydroalcoholic base is at least one antioxidant. The antioxidant can be any cosmetically acceptable antioxidant; examples of useful antioxidants for this purpose include cysteine and derivatives thereof, ascorbic acid and derivatives thereof, BHA, BHT, ferulic acid and derivatives thereof, grapeseed extract, pine bark extract, horseradish extract, hydroquinones, rosmarinic acid, caffeic acid, tocopherol and derivatives thereof, green tea extract, octyl, propyl and dodecyl gallates, uric acid and thiodipropionate derivatives. The preferred antioxidant is a natural antioxidant, for example, tocopherol or its derivatives. The antioxidant is normally present in the hydroalcoholic base in an amount of from about 0.5–10% by weight, preferably in an amount of from about 1–3%. With respect to both the UV absorbers and antioxidants, it will be recognized that the list is not exhaustive; numerous examples of both types of materials are well known to the skilled artisan, and other examples can also be found in, e.g., in the International Cosmetic Ingredient Handbook, Third Edition, CTFA, Washington, D.C., 1995, the contents of which are incorporated herein by reference.

The hydroalcoholic base can contain other optional components. For example, it is usually desirable to include in the base one or more emulsifiers to enhance the mixing of the components. Any emulsifier which is compatible with the components to be mixed, and which are useful in a hydroalcoholic system, can be used. An example of useful emulsifiers are alkoxylated alcohols, particularly glyceryl ester derivatives. The emulsifier component, if used, is preferably present in an amount of from about 0.5–15%, more preferably in an amount of from about 1–5%. The hydroalcoholic base may also contain one or more moisturizers, and these may be any which are compatible with the hydroalcoholic solvent system.

To prepare the base, the water soluble components are added directly to the water component, and mixed well; similarly, the non-water soluble components are added to the alcohol component, and also mixed well. The two phases are then combined, and mixed vigorously until a uniform mixture is achieved.

The hydroalcoholic base is added to a dry absorbent base. The principle component of the absorbent base is a porous bead which is capable of absorbing the liquid pigment-containing base but is not soluble therein, is free-flowing, and is also fairly heat-tolerant. Examples of particularly useful materials for this purpose are porous spherical silica materials. Preferred are porous silica beads with a particle size of 1–20 microns, more preferably from about 4–6 microns. In principle, the porous bead can be the sole component of the absorbent base. The liquid pigment base can be added directly thereto, and a stable pigment composition is obtained.

However, in order to make the composition more practical for use in makeup compositions, additional dry components are added to the porous bead before mixing with the liquid base. One preferred optional component is mica, which provides a useful opacity without whiteness, and also contributes to adhesion and lay-down of the product on the skin. Mica can be employed in the absorbent base in an amount of up to about 85%, preferably in amount of from about 70–80%, by weight of the total absorbent base.

Also desirable in the absorbent base is a hydrophobic coating for the bead, which will assist in preventing bleeding of the pigment from the bead once it has been absorbed therein. A preferred hydrophobic coating on the bead is formed by a polysiloxane. When employed, the coating can be used in an amount of about 5–20%, and preferably 5–10%, of the weight of the bead to be coated. When used in combination with these elements, the porous bead comprises from about 5–20% of the total weight of the absorbent base. To prepare the coated beads, the components are simply mixed together well, and then pulverized or ground together for a few minutes. Alternately, suitable precoated beads can be purchased commercially; an example of a particularly useful dimethyl polysiloxane coated bead is available from US Cosmetics, under the trade name SXI-5.

To prepare the final pigment composition, the liquid base is added to the prepared bead mixture, and mixed thoroughly. The mixture is then ground or pulverized for a few minutes. After the grinding, the material may still be wet; in such a case, the mixture is decanted of any standing liquid, and the remaining mass allowed to air dry or to heat dry in a suitable apparatus. The proportions in mixing the liquid base with the absorbent base are not critical, as the absorbent base will only absorb a certain amount of the liquid in any case. Although an excess of either base can be provided, approximately equal proportions, or a small excess of the absorbent base yields a particularly satisfactory result.

The compositions of the invention are quite stable over prolonged storage periods, under a variety of light and temperature conditions, with substantially no adverse effect on the appearance of the pigment. The compositions have also been tested for bleeding potential in various solvents; little or no bleeding of pigment occurs when added to either water or oil. Thus, the pigments compositions are eminently well suited for use in color cosmetics.

The pigment composition prepared as described above is ready to be added to a cosmetic base of choice. The composition can be used in any cosmetic base in which a pigment would be necessary or desirable, using standard methodology. For example, the pigment composition can be incorporated into wax-based products, such as lipsticks and lip glosses, fluid products(either aqueous or non-aqueous) such as foundations, cream eye shadows and blushes, and lotion and cream treatment, and powder products, such as face powder, powder blushes and powder eye shadows.

The invention is further illustrated in the following non-limiting examples.

EXAMPLES

I. Preparation of the Pigment Composition

| A. Natural color liquid base | |
|---|---|
| Component | Weight % |
| Denatured ethanol (SD-40B) | 30 |
| Benzonphenone-4 | 2 |
| Tocopherol | 2 |
| Panthenol | 2 |
| PEG-40 Hydrogenated Castor Oil | 2.5 |
| Deionized Water | QS |
| Beta-carotene | 9.5 |

The denatured alcohol is weighed out. Each of the benzophenone, tocopherol, panthenol, and PEG-40 hydrogenated castor oil components is added sequentially to the alcohol and mixed until dissolution before addition of the next ingredient. The deionized water is weighed out separately; the natural color is then added, mixed well and dissolved. The alcohol mixture is added to the water mixture, and then mixed vigorously until the mixture achieves a uniform consistency.

| B. Absorbent Base | |
|---|---|
| Component | Weight % |
| Mica | 80 |
| Silica bead | 18 |
| Dimethylpolysiloxane | 2 |

All three components are mixed together thoroughly, and then passed through a pulverizing/grinding procedure for two minutes in a laboratory Osterizer.

C. Pigment composition

The dissolved liquid base is added to an approximately equal weight of absorbent base, and mixed well. The mixture is then passed through the pulverizing/grinding procedure for four minutes. Any moisture remaining after the grinding procedure is removed by air- or heat-drying in an explosion-proof vessel.

II. Preparation of a Pressed Powder Base

| Component | Weight % |
| --- | --- |
| Mica | 45 |
| Talc | 14 |
| Silica | 20 |
| Lauryl lysine | 5.5 |
| Zinc Stearate | 2.28 |
| Methylparaben | 0.02 |
| Myristyl lactate | 3.5 |
| Cetyl lactate | 3.7 |
| Squalane | 3 |
| Triisostearin | 3 |

In a suitable vessel are combined mica, talc, silica, lauryl lysine, zinc stearate, and methyl paraben. The components are mixed well, then ground together for two minutes. The remaining ingredients are combined for a binding solution; these are mixed together separately, heated to 50° C. and mixed well until all ingredients are completely dissolved. The binding solution is then dripped slowly into the dry ingredients, mixed well, and ground for four minutes. To this base is added the prepared absorbent base, in a ratio of 70:30 powder base to prepared pigment-containing absorbent base. The components are mixed well and ground for four minutes. The material so prepared is then ready for pressing into an eyeshadow or blusher.

What I claim is:

1. A method for preparing a stable natural pigment-containing flowable powder comprising combining (a) a liquid hydroalcoholic base containing a natural pigment, a UV absorber, and an antioxidant, with (b) an absorbent base containing a porous bead, grinding the combined bases, and allowing the absorbent base to absorb the liquid base.

2. The method of claim 1 which includes the further step of drying the combined hydroalcoholic and absorbent bases.

3. The method of claim 1 in which the absorbent base also comprises mica.

4. The method of claim 1 in which the bead comprises a hydrophobic coating.

5. The method of claim 4 in which the hydrophobic coating is a polysiloxane.

6. The method of claim 1 in which the hydroalcoholic base also comprises an emulsifier.

7. The method of claim 1 in which the natural pigment is selected from the group consisting of annato extract, azulene, B-Apo-8-carotenal, beta-carotene, beet powder, canthaxanthin, caramel color, carrot oil, cochineal extract (carmine), cotton seed flour, ferrous gluconate, fruit juice, grape color extract, grape skin extract(ecociannina), paprika, riboflavin, saffron, titanium dioxide, turmeric, turmeric oleoresin, vegetable juice, chlorophyll, guaizulene, and red cabbage.

8. The method of claim 1 in which the UW absorber is selected from the group consisting of salicylates, para-amino benzoic acid(PABA) or derivatives thereof, amino benzoates, benzophenones, ferulic acid or derivatives thereof, digalloyl trioleate, cinoxate, cinnamates, and anthranilates.

9. The method of claim 1 in which the antioxidant is selected from the group consisting of cysteine and derivatives thereof, ascorbic acid or derivatives thereof, BHA, BHT, ferulic acid or derivatives thereof, grapeseed extract, pine bark extract, horseradish extract, hydroquinones, rosmarinic acid, caffeic acid, tocopherol or derivatives thereof, green tea extract, octyl, propyl or dodecyl gallate, uric acid and thiodiproprionate derivatives.

10. The method of claim 1 in which the hydroalcoholic base contains a benzophenone as UV absorber, and tocopherol or a derivative thereof as antioxidant.

11. The method of claim 1 in which the absorbent base comprises a porous silica bead, a polysiloxane coating, and mica.

12. A pigment composition prepared according to the method of claim 1.

13. A pigment composition prepared according to the method of claim 10.

14. A pigment composition prepared according to the method of claim 11.

15. A stable natural pigment-containing flowable powder composition comprising an absorbent base containing a porous bead, into which has been absorbed a hydroalcoholic base containing a natural pigment, an UV absorber and an antioxidant.

16. The composition of claim 15 in which the bead is a silica bead.

17. The composition of claim 16 in which the bead comprises a hydrophobic coating.

18. The composition of claim 17 in which the absorbent base also comprises mica.

19. The composition of claim 15 in which the natural pigment is selected from the group consisting of annato extract, azulene, B-Apo-8-carotenal, beta-carotene, beet powder, canthaxanthin, caramel color, carrot oil, cochineal extract(carmine), cotton seed flour, ferrous gluconate, fruit juice, grape color extract, grape skin extract(ecociannina), paprika, riboflavin, saffron, titanium dioxide, turmeric, turmeric oleoresin, vegetable juice, chlorophyll, guaizulene, and red cabbage.

20. The composition of claim 15 in which the UV absorber is selected from the group consisting of salicylates, para-amino benzoic acid(PABA) or derivatives thereof, amino benzoates, benzophenones, ferulic acid or derivatives thereof, digalloyl trioleate, cinoxate, cinnamates, and anthranilates.

21. The composition of claim 15 in which the antioxidant is selected from the group consisting of cysteine and derivatives thereof, ascorbic acid or derivatives thereof, BHA, BHT, ferulic acid or derivatives thereof, grapeseed extract, pine bark extract, horseradish extract, hydroquinones, rosmarinic acid, caffeic acid, tocopherol or derivatives thereof, green tea extract, octyl, propyl or dodecyl gallate, uric acid, and thiodiproprionate derivatives.

22. The composition of claim 15 in which the absorbent base comprises a porous silica bead, a polysiloxane coating and mica, and the hydroalcoholic base comprises a benzophenone as UV absorber and tocopherol or a derivative thereof as antioxidant.

23. A cosmetic composition comprising the pigment composition of claim 12.

24. A cosmetic composition comprising the pigment composition of claim 13.

25. A cosmetic composition comprising the pigment composition of claim 14.

26. A cosmetic composition comprising the pigment composition of claim 15.

27. A cosmetic composition comprising the pigment composition of claim 22.

28. A cosmetic composition comprising the pigment composition of claim 15 combined with a pressed powder base.

* * * * *